United States Patent
Erbel et al.

(10) Patent No.: US 6,508,787 B2
(45) Date of Patent: Jan. 21, 2003

(54) SYSTEM FOR ACTIVELY SUPPORTING THE FLOW OF BODY FLUIDS

(75) Inventors: Reimund Erbel, Essen; Gerald Voegele, Magstadt; Thomas Weisener, Ditzingen; Andreas Maya, Neubulach; Carlo Bark, Schoerzingen; Mark Widmann, Boennigheim, all of (DE)

(73) Assignee: Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 0 days.

(21) Appl. No.: 09/043,699

(22) PCT Filed: Sep. 26, 1996

(86) PCT No.: PCT/DE96/01834

§ 371 (c)(1),
(2), (4) Date: May 26, 1998

(87) PCT Pub. No.: WO97/11737

PCT Pub. Date: Apr. 3, 1997

(65) Prior Publication Data

US 2001/0018569 A1 Aug. 30, 2001

(30) Foreign Application Priority Data

Sep. 26, 1995 (DE) .......................... 195 35 781

(51) Int. Cl.[7] .................................. A61M 1/00

(52) U.S. Cl. ..................... 604/151; 604/96.01; 600/16; 417/205

(58) Field of Search ..................... 604/93, 96, 97–98, 604/101, 102, 131, 151, 96.01, 101.01, 101.02, 101.03, 101.04, 101.05, 102.01–102.03, 97.01, 98.01, 919; 417/1–2, 3, 16, 65–67, 201, 205; 600/16, 18; 606/192, 194

(56) References Cited

U.S. PATENT DOCUMENTS

| 4,625,712 A | | 12/1986 | Wampler ................... 128/1 D |
| 4,688,998 A | * | 8/1987 | Olsen et al. ................ 415/900 |
| 4,790,315 A | | 12/1988 | Mueller, Jr. et al. ........ 128/344 |
| 4,877,031 A | | 10/1989 | Conway et al. ............. 128/344 |
| 4,908,012 A | * | 3/1990 | Moise et al. ................ 415/900 |
| 4,919,647 A | * | 4/1990 | Nash .......................... 415/900 |

(List continued on next page.)

FOREIGN PATENT DOCUMENTS

| DE | 3713 061 A1 | 11/1987 |
| DE | 3621 350 C2 | 1/1988 |
| DE | 4124 299 A1 | 1/1992 |
| DE | 44 21 920 A1 | 1/1995 |
| EP | 277 367 A1 | 8/1988 |
| EP | 203 945 B1 | 8/1989 |
| EP | 353 889 A1 | 2/1990 |
| EP | 344 201 B1 | 7/1991 |
| WO | 93/17748 | 9/1993 |

*Primary Examiner*—Brian L. Casler
*Assistant Examiner*—LoAn H. Thanh
(74) *Attorney, Agent, or Firm*—Heller Ehrman White and McAuliffe

(57) ABSTRACT

The present invention relates to a device for actively supporting the flow of body fluids, comprising an artificial flow guide system (10) with an operational area into which a pump (1) is embedded in such a way that it can transport blood from at least one inlet opening (3) situated in the guide system to at least one outlet opening (4) situated in the guide system; a flexible feed hose (5) connected to the flow guide system; an energy or force transmission line (6) which is guided through the interior of the flexible feed hose and which, when the device is in the operational state, transmits energy or force substantially continuously to the pump from a drive unit for the extracorporeal generation of this energy or force.

22 Claims, 11 Drawing Sheets

U.S. PATENT DOCUMENTS

| | | | |
|---|---|---|---|
| 4,964,864 A | * 10/1990 | Summers et al. | 623/3 |
| 5,112,349 A | * 5/1992 | Summers et al. | 623/3 |
| 5,163,910 A | * 11/1992 | Schwartz et al. | 604/151 |
| 5,169,378 A | * 12/1992 | Figuera | 600/16 |
| 5,295,959 A | 3/1994 | Gurbel et al. | 604/96 |
| 5,318,531 A | * 6/1994 | Leone | 604/96 |
| 5,328,471 A | * 7/1994 | Slepian | 604/101 |
| 5,334,154 A | 8/1994 | Samson et al. | 604/102 |
| 5,368,566 A | * 11/1994 | Crocker | 604/101 |
| 5,370,617 A | 12/1994 | Sahota | 604/102 |
| 5,569,184 A | * 10/1996 | Crocker et al. | 604/53 |
| 5,707,218 A | * 1/1998 | Maher et al. | 417/356 |
| 5,749,855 A | * 5/1998 | Reitan | 604/151 |
| 5,776,190 A | * 7/1998 | Jarvik | |
| 5,888,241 A | * 3/1999 | Jarvik | |

* cited by examiner

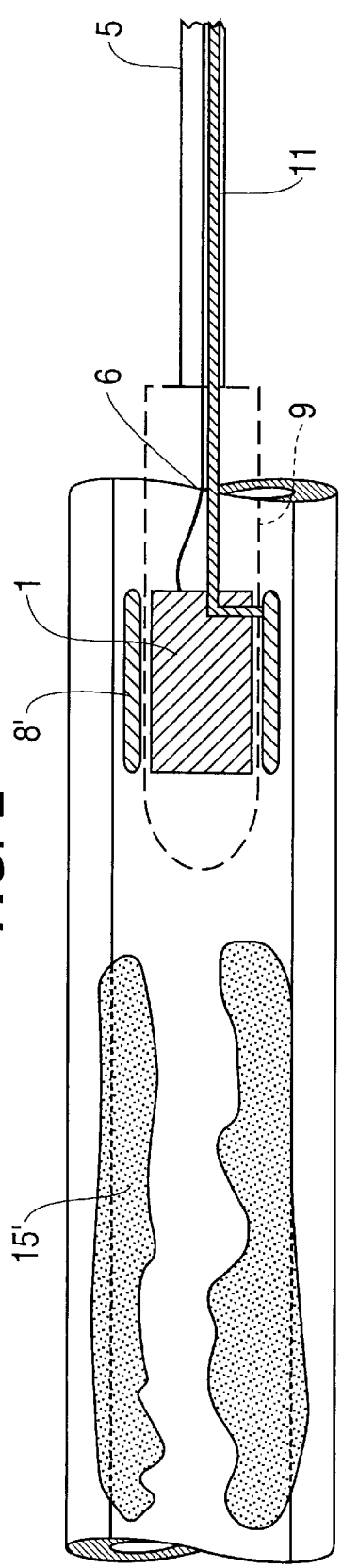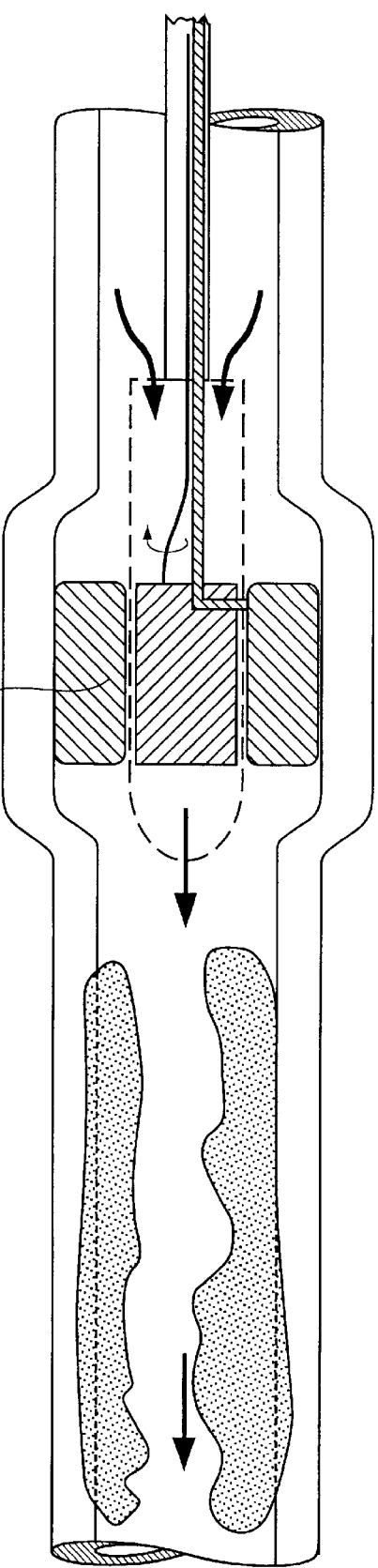

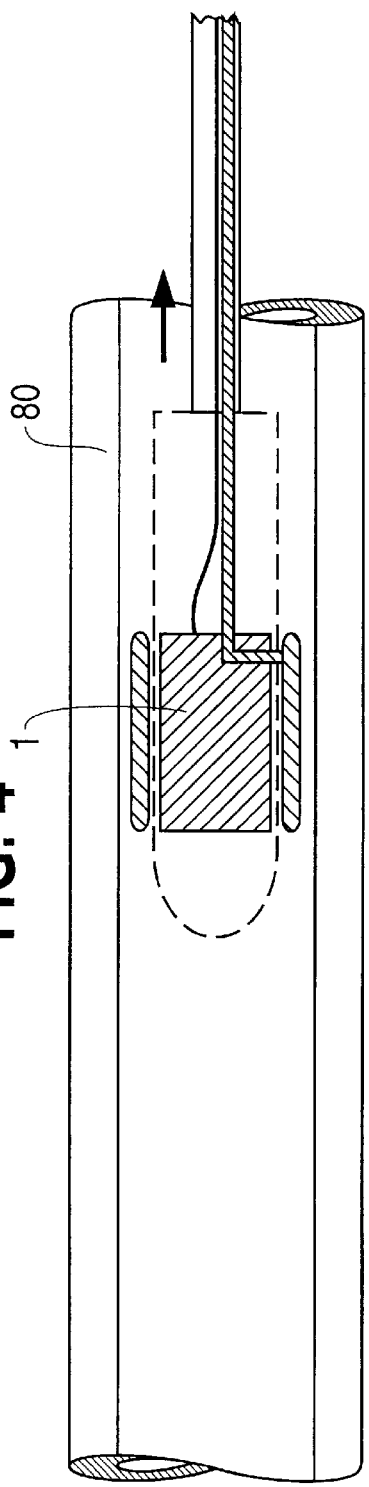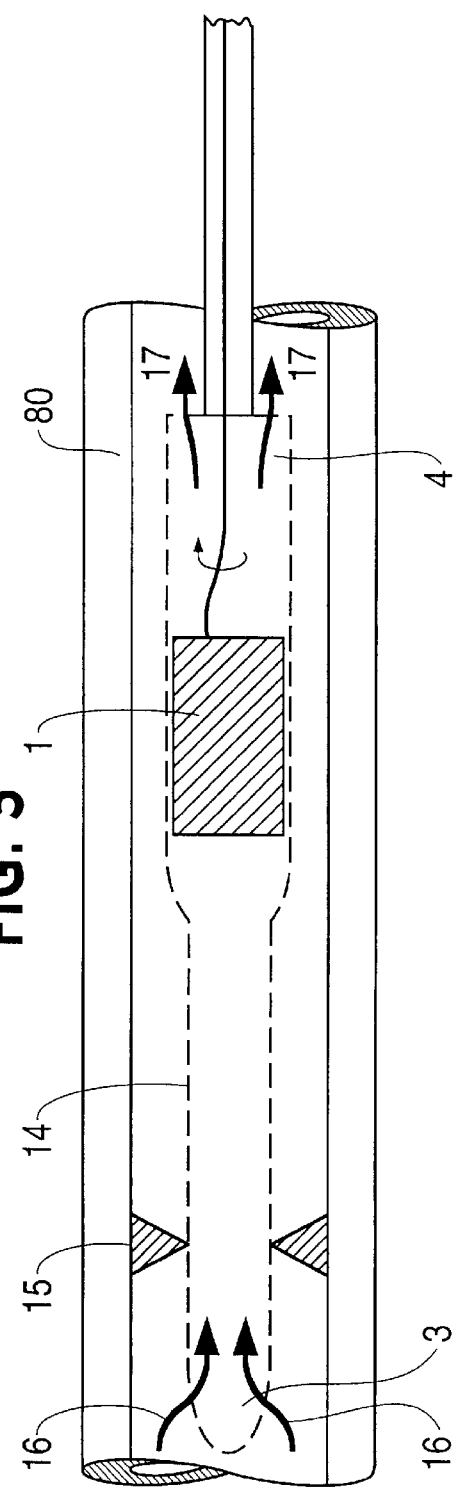

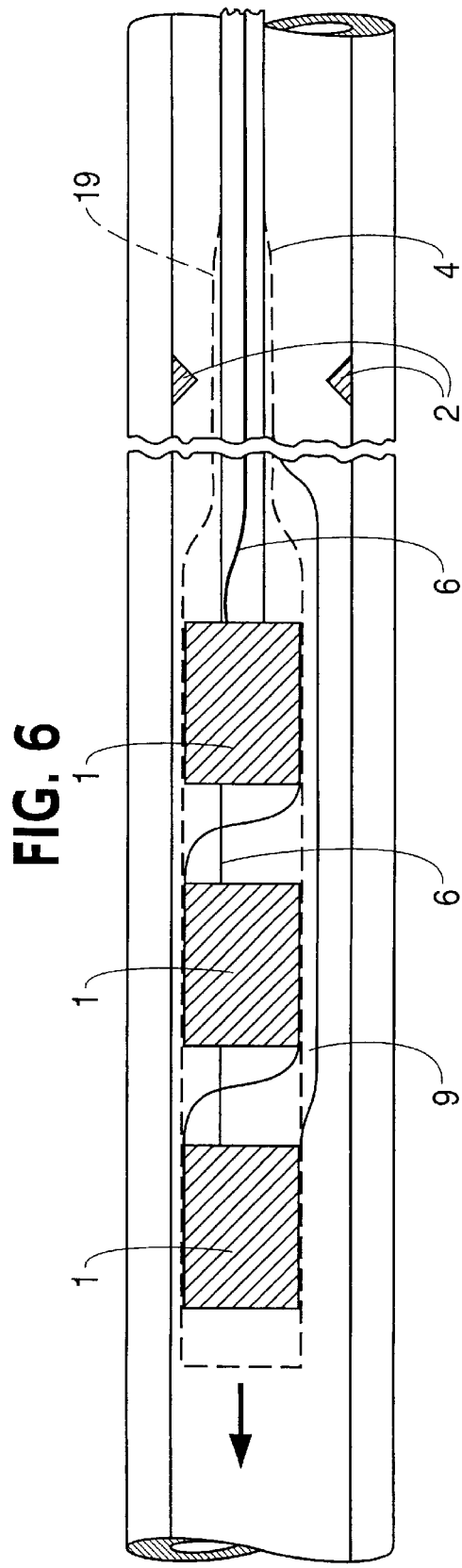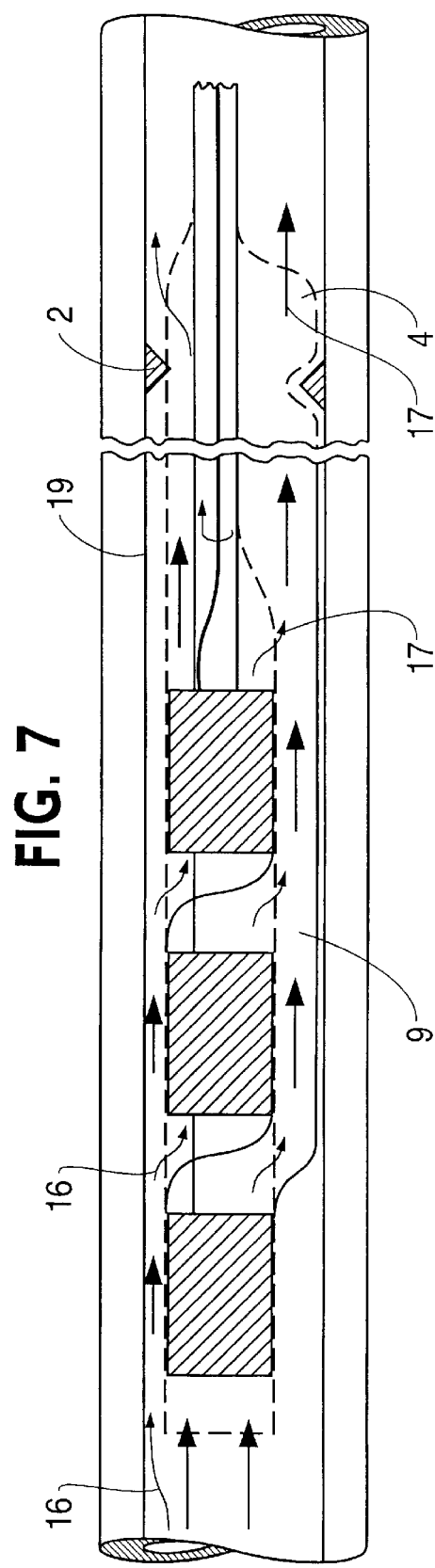

SYSTEM FOR ACTIVELY SUPPORTING THE FLOW OF BODY FLUIDS

BACKGROUND OF THE INVENTION

1. Field of the Invention

The present invention concerns the field of medical engineering and relates in particular to those systems with which invasive microsurgery, invasive drug therapy, circulatory support, dilation of vascular systems, and the like, can be carried out.

In recent years, there have been enormous advances in the treatment of organs which carry fluids, particularly those of the circulatory system. The development of catheters and invasive surgery instruments makes it possible to avoid intricate operations which impose a physical burden on the patient, and to rapidly and effectively treat acute states such as sudden cardiac arrest in cases of cardiogenic shock. Common to all these methods is the fact that the microsurgery instrument used is advanced to the "insertion" site through pathways which carry body fluid. Naturally, during its insertion, it greatly obstructs the flow of the body fluid there through the vessel in question, or even completely suppresses this flow.

2. Description of Related Art

Regarding the use of dilation catheters, to which the present invention is applicable inter alia, this problem has long been recognized and has prompted a number of proposals. Common to most of these proposals is that a blood flow guide system is provided inside the catheter, wherein the system has a proximal inlet and a distal outlet for blood flowing through it. These permit a passive, relatively small blood stream upon balloon dilation, brought about by the pressure difference prevailing at the dilation site (so-called autoperfusion catheter). Although the period of use of such an autoperfusion catheter is prolonged by this measure, it is still very limited because the decrease in the delivery of blood to the distally situated tissue can very quickly lead to an inadequate supply, with irreversible consequences.

An improvement was hoped for from those systems in which, with the aid of a pump, blood is actively transported through a lumen of the catheter from another vessel, for example the femoral artery (so-called active hemoperfusion catheter). However, this again has the disadvantage that a further vessel has to be tapped and the blood has to be brought to the required pressure by means of an extracorporeal, mechanical high-pressure pump and then delivered to the dilation catheter. Such a device is disclosed in the European Patent Application bearing the publication number 277 367 A1.

A further proposal envisages blood being suctioned proximally in pulses with the aid of a flap valve and of a liquid column, which can be advanced and retreated and is moved with an extracorporeal plunger, and this blood being ejected distally at the system pressure through an opening, with possible backflow being prevented by a distal ball valve. This device is already susceptible to failure because of the flap valve, it is of a complicated construction, demands the continuous supply of fresh saline solution, because the force-transmitting saline solution is not sealed off from the blood flow guide system, and can only be used in those cases where the catheter can be introduced into the relevant vessel in the direction of flow. A further disadvantage is the noncontinuous blood transport through the area of the stenosis. Such a device is shown in the European Patent Application bearing the publication number 353 889 A1.

A further attempted solution concerns the field of heart catheters. Here, it has been proposed to support a patient's circulatory system with the aid of an intra-ventricularly expanding auxiliary pump for supporting the heart. In this pump, an outer chamber with a double wall structure can be pressurized in such a way that it expands within the ventricle, in so doing becomes rigid and adapts to the ventricle wall. An inner balloon is inflated in pulses, as a result of which the diastole and systole of the heart are alternately imitated.

However, it has never been possible to achieve clinical acceptance of such a device.

SUMMARY OF THE INVENTION

The present invention is based on the object of making available a device which can be applied in all those cases in which the use of a medical instrument is necessary whose insertion into the body obstructs the flow of a body fluid. In this connection, the device is to be constructed in such a way that the use of this instrument is nonetheless possible, or is made easier, or its possible duration of use is extended. Although the insertion in blood vessels is of course the primary concern here, because invasive microsurgery, circulatory support and the like are of great importance, the invention is not however restricted to this. It is also suitable for use in lymph, bile or, if desired, liquor, for example in invasive gallbladder operations in which the transport of the bile should not be interrupted.

According to the invention, the aforementioned object is achieved by the provision of a device for actively supporting the flow of body fluids.

The design and material of the artificial flow guide system, and its additional fittings, will depend on the envisaged application. For example, it is possible to employ the materials and dimensions used in conventional dilation catheters. Designs which are particularly suitable for special applications are described in detail below.

The artificial flow guide system has an operational area in which a pump is embedded in such a way that it can transport blood from at least one inlet opening situated in the guide system to at least one outlet opening situated in the guide system. The expression "embedded" is here intended to signify that between the pump and the wall of the operational area there is as little distance as possible, preferably no distance, i.e. that the pump bears against the wall with substantial or complete sealing. In this arrangement, in specific embodiments, the pump can be driven in such a way that the body fluid can be transported in both directions, so that the device can be introduced both in co-current and counter-current with the flow of fluid through the vessel.

The design of the inlet and outlet openings will in each case depend on the type of application. The design can range from small circular openings in the side wall (e.g. arranged proximally as inlet opening), a single opening at the distal end (e.g. as outlet for a dilation catheter) or, e.g., a plurality of openings on one or both sides, right through to net-like and grid-like structures in the wall of the flow guide system.

The delivery of fluid through the pump can likewise be variable. Thus, the fluid to be conveyed can enter the flow guide system on the suction side of the pump and leave on the delivery side (at the distal end of the guide system, or else already further proximally). Alternatively, it can enter and leave on the delivery side.

The flow guide system itself must have such great flexibility that both its advance and also, and in particular, its function are possible within an optionally relatively strongly curved flow section of the corresponding blood vessel or of other fluid-carrying vessels. In this connection, preferably, the flow guide system is particularly flexible at least in a distal segment. In one embodiment, the flow guide system has a more rigid proximal segment and a more flexible distal segment. The proximal segment can have the same diameter as the distal segment, although it can also have a greater inner width. If the pump is arranged in this proximal area, it is better supported by the more rigid casing. In the case of the greater diameter of the proximal section, it is possible to incorporate a larger pump (with an improved pumping capacity). This is particularly of advantage when a very flexible, relatively long distal catheter segment is provided, in order, for example, to dilate those vessels which supply blood to the heart. In this case, the catheter can be advanced through the relatively large vessels to a point close to the area to be treated; in the treatment position, the very flexible distal segment of the flow guide system projects into the stenosed area and dilates this, for example with the aid of inflatable balloons, while the more rigid, larger catheter segment lies in a blood vessel area which has a greater diameter.

A flexible feed hose is connected to the flow guide system. The flexible feed hose can in this case be worked in one piece with or connected integrally to the flow guide system, although positively engaged or frictionally engaged connections or adhesive bond connections, or the like, are of course also possible.

In one embodiment of the invention, the feed hose too can have a rigid segment. It can also be more rigid overall than the flow guide system. If a relatively rigid segment such as this is present, or if a feed hose such as this is chosen which is more rigid overall than the flow guide system, in one embodiment of the invention said segment or the distal end of the feed hose is pushed over the proximal, flexible part of the flow guide system (or is connected securely thereto). In this embodiment, the proximal part of the flow guide system is therefore embedded in a more rigid segment, preferably in a sealing manner. Depending on the purpose for which the flow guide system is intended, the pump can in this case either be embedded in the area surrounded by the more rigid segment (that is to say on the proximal side) or can be arranged in the distal area. An advantage of its being embedded in the proximal area is here once again that the pump is better supported by the more rigid "outer skin".

The flexible feed hose as such is designed as a function of its application. It should preferably be of such a length that the distal end, with respect to the pump, still lies outside the body, at the furthest possible distance from the admission opening, during use.

An energy or force transmission line is guided through the interior of this feed hose. This line must be designed such that, when the device is in the operational state, it can transmit energy or force to the pump substantially continuously from a drive unit, which is outside the body in the operational state, unless it is the drive for a so-called ram pump or the like which is moved alternately forward and backward in the axial direction and is rotated simultaneously or nonsimultaneously, continuously or noncontinuously.

The aforementioned drive forms for the pump have several advantages. They permit the use of a large number of different pumps, so that, depending on the purpose for which the instrument is intended to be used, the appropriate pump can be chosen. It is possible in particular—but not exclusively—to drive pumps which permit a substantially continuous delivery of the body fluid, which ought to be preferable in most cases. If noncontinuous delivery is desired, then, according to the invention, it is possible to avoid fluid entering the pump from the lumen of a fluid drive column and thereby escaping to the body fluid if this is undesirable, and, in so doing, involuntarily increasing the volume of fluid surrounding the pump. Moreover, the use of valves in the pump area should in most cases be unnecessary. The drives according to the invention permit an extremely convenient handling of the medical instruments, since said admission line matches the curves of the flexible feed hose. The omission of an extracorporeal pump, which for its part has to be driven mechanically and causes losses of liquid column into the system, is likewise advantageous.

Those embodiments which have a substantially continuous drive are preferred since the extracorporeal drive means are very easy to handle. The expression "substantially continuous" is intended to signify that the transport of energy or force is macroscopically continuous. This expression is intended to encompass system-related or technically induced minimal variations (or the use of alternating current or currents with microscopic changes of individual parameters). A preferred embodiment of this kind is also the transmission of force with the aid of a flexible mechanical shaft. Other continuous drive possibilities which may be mentioned by way of example here are: the electrical drive of micromotors, which in turn drive the pump or an electrical drive of pumps such as diaphragm pumps and the like.

In one preferred embodiment, the lumen of the artificial flow guide system which is provided for the flow of body fluid is sealed off from the flexible feed hose. This prevents backflow into the admission tubing, without having to work with valves.

A guide system is normally provided on one side of the device, which guide system is mostly referred to as a guide wire and which can be easily deformed, but should have a certain rigidity in the axial direction. If necessary, this can also be present as an independent subsystem, which is guided in a separate lumen of the catheter.

The pump itself can be chosen freely, and the choice will depend on the purpose for which it is intended. In most cases, continuously operating pumps are preferred. Here, miniaturized gear pumps or vane pumps are possible, while centrifugal pumps, hose pumps, diaphragm pumps or balloon pumps are further possibilities. A noncontinuously operating pump is the ram pump.

The dimensions of the pump are of course also dependent on the purpose of use. Thus, a heart catheter pump will probably have greater dimensions than pumps for dilation catheters for expanding very small vessels. All dimensions from several cm down to the mm range, or even lower, are conceivable here.

The above-described device is suitable for use in many types of medical systems, some of which are described in particular by way of example hereinbelow. Here, the normal terms for the corresponding devices are also used, without the device according to the invention thereby being limited to the forms of these instruments which are usual today. The above explanations are of course applicable in each case to these embodiments.

BRIEF DESCRIPTION OF THE DRAWINGS

FIG. 2 is an explanatory illustration of how the catheter shown in FIG. 1 can be used for bloodstream support.

FIG. 3 is an explanatory illustration of how the catheter shown in FIG. 1 can be used for bloodstream support.

FIG. 4 is an explanatory illustration of how the catheter shown in FIG. 1 can be used for bloodstream support.

FIG. 5 is a schematic illustration of a modification of the catheter shown in FIG. 1.

FIG. 6 is a schematic illustration of a modification of the catheter shown in FIG. 1.

FIG. 7 is a schematic illustration of a modification of the catheter shown in FIG. 1.

DETAILED DESCRIPTION OF THE PREFERRED EMBODIMENTS

Figure 1:
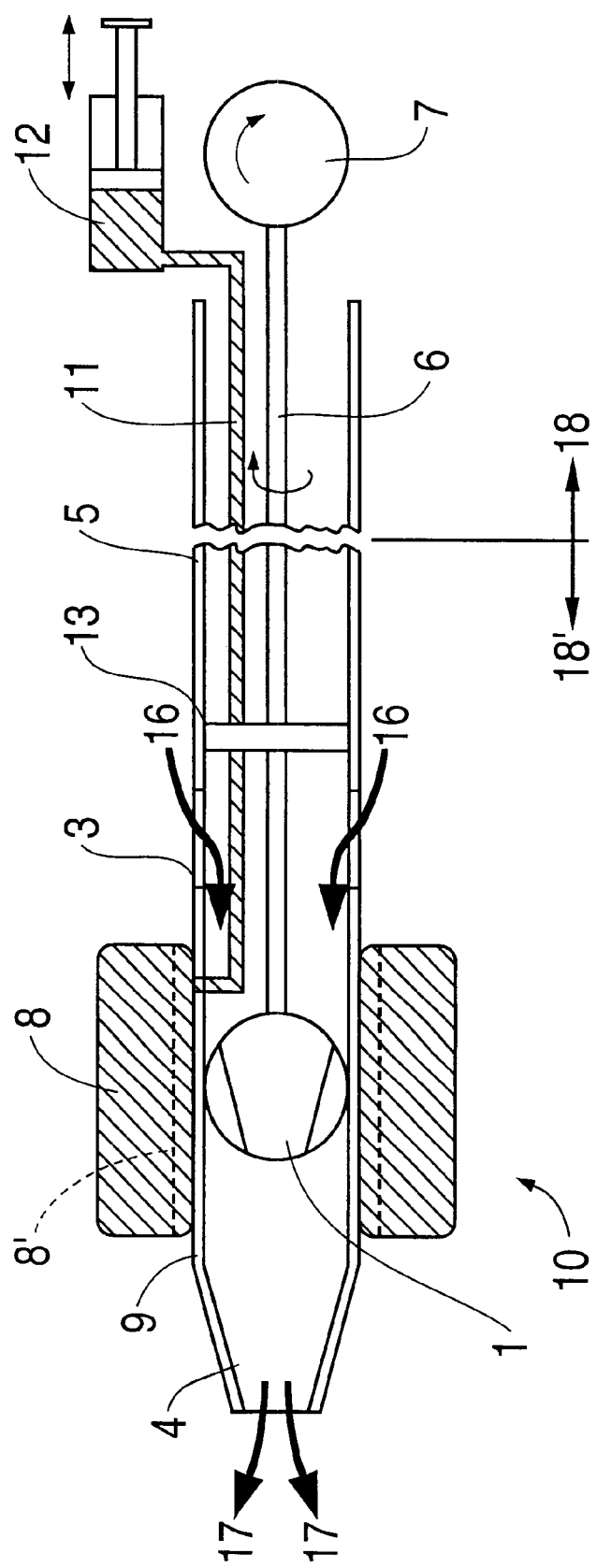
FIG. 1 is a schematic illustration of a catheter according to an embodiment of the present invention.

Illustrative Field of Application "Active Bloodstream Support"

A field of application for instruments based on such devices is, for example, both the total circulatory support, which is used in particular for supporting the circulation of patients with serious cardiogenic shock, and the support of the bloodstream in narrowed vessel areas with local ischemia, e.g. in embolisms, stenoses, occlusions, strictures, thromboses, ARDS (adult respiratory distress syndrome) of the lungs, etc. The invention can also be applied to heart catheters.

The use of mechanical cardiac support systems for total circulatory support may be considered, inter alia, in cases of sudden cardiac arrest, cardiogenic shock, severe coronary ischemia and high-risk PTCA (percutaneous transluminal coronary angioplasty).

The mechanical circulatory support is performed in the prior art using a number of systems which differ fundamentally from a technical point of view, e.g. by means of intra-aortic counterpulsation (IABP), the femoro-femoral bypass with magnetic centrifugal pumps, ventricle support by means of centrifugal pumps, roller pumps and thoracotomies, the heterotopic artificial ventricle (VAD), the total artificial heart (TAH), implantable turbine pumps (hemopump), intraventricularly expanding auxiliary pumps, and perfusion catheters.

Some disadvantages of perfusion catheters in current use have already been mentioned above. In addition, for the use of the (passive) autoperfusion catheter, it is necessary to have a mean arterial pressure of <90 mmHg so that an adequate blood flow (approximately 50 to 60 mml/min) can be maintained. In addition, these catheters are rigid and the balloon profile is long, so that these systems are unsuitable as primary instruments in narrow lesions or curved vessels.

The active hemoperfusion catheters are for their part admittedly more flexible and shorter than the usual autoperfusion catheters. In addition to the disadvantages mentioned above, it should also be noted here that operating with catheters of this kind is very time-consuming, involves additional costs and is limited to a maximum bloodstream of approximately 50 mml/min.

The coronary retroperfusion catheters and their disadvantages have also already been mentioned above. In sinus retroperfusion, arterial blood is delivered to the myocardium via the coronary sinus during the diastole.

The limits of conventional bloodstream support systems are therefore to be seen in the fact that the duration of the circulatory support is in most systems limited, the systems often demand a more major intervention, for example the opening of the thoracic cage, and in some cases are extremely costly. In "small" vessels (10 to 2 mm), only very small flows (maximum of 50 mml/min) can be achieved. Some of the aforementioned systems cause fairly major trauma; they can only be used in the context of extensive interventions.

It is therefore proposed to use, in this field, devices according to the present invention, if appropriate in further special embodiments which have already been mentioned above. In doing so, the bloodstream can be actively supported in a wide variety of diagnoses. Areas of application are, for example, bloodstream support in cases of sudden cardiac arrest, cardiogenic shock, severe coronary ischemia and high-risk PTCA, in which the complete circulation must be maintained, moreover in cases of embolisms, stenoses, occlusions, strictures and thromboses in peripheral arteries, in which only a local blood flow disturbance is to be remedied, and similar cases. As a result of the active maintenance of the bloodstream during disease-induced closure of a damaged vessel area, damage to the organs or tissue areas in question is minimized.

The bloodstream support catheter according to the invention will be explained below principally with reference to FIG. 1 and further figures, although variable embodiments are of course possible, some of which have already been described above. The devices for actively supporting the bloodstream are also often referred to below as "bloodstream support catheter" or simply "catheter". The catheter has a front part which is here referred to as the artificial flow guide system 10. Embedded in it is a pump 1 which, in a preferred embodiment, can be operated in both directions depending on the nature of the vectorial component, so that the catheter can be advanced to its "working site" both in the direction of flow and against the direction of flow in the vessel. The type of pump can be chosen freely; thus, for example, miniaturized gear pumps or vane pumps, centrifugal pumps, hose pumps, diaphragm pumps or balloon pumps are possible. Continuously feeding pumps are preferred. The pump can be chosen in different sizes, with correspondingly variable pumping capacity, for use in different vessel areas.

On the suction side of the pump there is at least one inlet opening 3 for inflowing blood 16; on the delivery side there is at least one outlet opening 4 for outflowing blood 17. The position, form, number and shape of the openings are variable and depend on the envisaged use. In this respect, reference should again be made to the more general statements. The housing 9 of the flow guide system can also be designed as a cage or netting (FIG. 2), particularly if the pumping capacity is chosen such that, in the case of openings which are too narrow, their cross section has a limiting effect on the output of the device. The artificial flow guide system 10 in FIG. 1 is connected integrally to the flexible feed hose 5. The energy or force transmission line 6 runs as far as the pump 1 through the interior of the feed hose 5 from a drive unit 7—not necessarily forming part of the present invention—which, when the catheter is in the operating state, is situated outside the body. The embodiment in FIG. 1 also shows a seal 13 according to the present invention, with which seal the lumen of the artificial flow guide system is sealed off from the flexible feed hose. The arrow 18' relates to that part of the catheter which passes into the body, the arrow 18 to those parts which remain outside the body.

In one specific embodiment, the bloodstream support catheter additionally comprises at least one shutoff balloon (represented in FIG. 1 in the nonpressurized state (8') and the pressurized state (8)). This balloon is used to obtain a sealing function between system and blood vessel and thus to reduce the pump power loss in those cases where the catheter is not sufficiently sealed off by the elastic vessel itself. The shutoff balloon 8 can be "inflated" with the aid of a gas or a liquid which can be introduced via a line 11, namely with the aid of a pressure generation arrangement 12, e.g. a balloon pump.

The flexible feed hose 5 connected to the artificial flow guide system, and the energy or force transmission line arranged therein, has already been described in detail above; the general and specific aspects which were set out there do of course also apply to the bloodstream support catheter.

FIGS. 2 to 4 explain how the catheter can be used: during bloodstream support, the operational area of the catheter is placed in the vessel 80 which is to be supported (FIG. 2). When using a shutoff balloon 8', the latter is expanded 8 in order to shut off the vessel area as much as possible. The pump in this case maintains the stream of fluid between the separated vessel areas (FIG. 3). After treatment, the balloon is made smaller and the catheter is removed again. 15' represents an obstruction, e.g. a thrombus.

In one specific embodiment, two or more pumps can be present in the artificial flow guide system 10. These pumps can be arranged in a cascade configuration, for example, and are preferably coupled in parallel with one another in order to increase the output accordingly. With this embodiment, it is possible to generate volume flows which exceed the pumping volume of a single pump, particularly if the diameter of the vessel receiving the catheter makes it necessary to work with very small pumps. A specific embodiment, with in this case three pumps arranged one after the other, is represented in FIGS. 6 and 7. In the embodiment shown, the distal end of the artificial flow guide system 10 is also designed differently than in FIG. 1: distally with respect to the last pump, it is here designed as a flexible outflow tubing 19 which, in the nonpressurized state, has a smaller diameter than in the area in which the pumps are situated. Simple insertion of the catheter is made possible in this way, also in the area of severe constrictions 2 (deposits, stenoses, constrictions caused by the geometry of the vessels, etc.). The outlet openings(s) 4 of the outflow tubing are situated at its distal end. If blood 16, 17 is now delivered through the lumen of the catheter with the aid of the pump, the tubing of the artificial flowguide system 10 is expanded so that it bears sealingly around the constriction 2 (see FIG. 7). The flexibility of the outflow tubing can be obtained in various ways, for example by means of an extremely easily expandable material, or else by the fact that the tubing in the "rest state" is folded or otherwise rolled up. Thus, for example, it can be placed/wound around an additionally present guide wire (not shown), or it can itself serve as a guide if there is sufficient rigidity in the axial direction.

Of course, the various construction elements, as represented in FIGS. 6 and 7, are not necessarily always present at the same time in one and the same embodiment.

The suction area of the artificial flow guide system can, if so required, be at a greater distance from the pump, in which case the flow guide system can be designed in the intermediate area as a flexible or rigid tubing extension 14. Such an embodiment is represented by way of example in FIG. 5. In the embodiment which is represented, the pump delivers the blood in the reverse direction 16, 17, compared to FIG. 1, so that the suction side is directed toward the distal end of the catheter. The diameter of the tubing extension 14 is here smaller than the catheter diameter in the area of the pump, so that lumens of very small diameters, or behind constrictions, are accessible and the treatment can be performed in very narrow vessels or near the heart. In such an embodiment, the catheter could also be advanced through a heart valve 15 into the heart. Also, with such an embodiment, blood can be suctioned through lumens which present stronger curves than can be performed by the catheter. The blood is then in each case suctioned behind the constriction or directional change and expelled again in the outlet area 4.

Illustrative Field of Application "Dilation Catheters"

Dilation catheters have been developed in particular for the treatment of stenoses in blood vessels.

Dilation catheters without a bloodstream guide system can remain in the expanded state for a maximum of 20 to 30 seconds, since the inflation of the balloon in the case of the vital myocardium interrupts the blood-stream and results in a disturbance in the blood supply to the heart. Consequences of longer dilation include cardiac dysrhythmias, severe angina pectoris and a drop in blood pressure. If the dilation is performed in the proximal area, i.e. near the ostium, cardiogenic shock syndromes may occur, which are life-threatening. A number of techniques have therefore been developed which are intended to overcome this disadvantage. These include bypass operations, rapidly and slowly rotating systems with equipped milling head, implants for enlarging the vessel interior (stents), removal of deposits with the aid of laser angioplasty, ultrasound, adherectomy and autoperfusion catheters, which permit a passive, relatively small bloodstream upon balloon dilation.

All these methods to some extent require a massive intervention, some of them can only be used with extremely complex medical engineering, and in some cases they are simply unsatisfactory because the residual volume of blood is insufficient to prevent iatrogenic disturbances.

It is therefore proposed to use, in this field, devices according to embodiments of the present invention, if appropriate in further special embodiments which have already been mentioned above. During treatment-induced closure of vessel areas, embodiments of the present invention allow the bloodstream to be artificially maintained or allows such a bloodstream to be generated. In this way, with the aid of these devices, longer treatment times are made possible, which mean an important procedural improvement in terms of the stabilization of the prepared vessel cross section and, consequently, the length of time before the next necessary operation. At the same time, the risk of the treatment can be substantially reduced. This can be deduced in particular from a study relating to the use of autoperfusion catheters, which study has established a reduction in the number of sudden vessel closures and immediate bypass operations, with the bloodstream being maintained. The invention permits further improvements here.

The dilation catheter according to the invention will likewise be explained below principally with reference to FIG. 1 and further figures, although variable embodiments are of course possible, some of which have already been described above. The dilation catheter too has a front part which is referred to as the artificial flow guide system 10. Embedded in it is at least one pump 1 which, in a preferred embodiment, can be operated in both directions depending on the nature of the vectorial component, so that the catheter can be advanced to the constriction both in the direction of flow and against the direction of flow in the vessel. The type of pump can also be chosen freely here; the miniaturized gear pumps or vane pumps, centrifugal pumps, hose pumps, diaphragm pumps or balloon pumps already mentioned above are especially possible here. Continuously feeding pumps are preferred. The pump can be chosen in different sizes, with correspondingly variable pumping capacity, for use in different vessel areas.

On the suction side of the pump there is at least one inlet opening 3 for inflowing blood 16; on the delivery side there is at least one outlet opening 4 for outflowing blood 17. The position, form, number and shape of the openings are variable and depend on the envisaged use. In this respect, reference should again be made to the more general statements. The housing 9 of the flow guide system can also be designed as a cage or netting (FIG. 2), particularly if the pumping capacity is chosen such that, in the case of openings which are too narrow, their cross section has a limiting effect on the output of the device. The artificial flow guide system 10 in FIG. 1 is connected integrally to the flexible feed hose 5. The energy or force transmission line 6 runs as far as the pump 1 through the interior of the feed hose 5 from a drive unit 7—not necessarily forming part of the present invention—which, when the catheter is in the operating state, is situated outside the body. The embodiment in FIG. 1 also shows a seal 13 according to embodiments of the present invention, with which seal the lumen of the artificial flow guide system is sealed off from the flexible feed hose. The arrow 18 relates to that part of the catheter which passes into the body, the arrow 18 to those parts which remain outside the body.

A shutoff balloon (8, 8') is arranged around the artificial flow guide system. In this arrangement, in one embodiment as shown in FIG. 1, the pump can be arranged in the area of the artificial flow guide system which is covered by the outer balloon, although it can also have another location in relation to the balloon (or vice versa). The balloon 8 is used to expand a narrowed vessel. It can be "inflated" with the aid of a gas or a liquid which can be introduced via a line 11, namely with the aid of a pressure generation arrangement 12, e.g. a balloon pump.

Of course, the invention is not limited to dilation catheters with only one pump or with only one balloon. Regarding the arrangement of several pumps, what has already been stated above once again applies. It is also possible, depending on the intended use, to provide several balloons. The location and positioning of pump in relation to balloon are in this case variable.

The flexible feed hose 5 connected to the artificial flow guide system, and the energy or force transmission line arranged therein, and different flexibilities in different segments of the flow guide system and between flow guide system and feed hose, have already been described in detail above; the general and specific aspects which were set out there do of course also apply to the dilation catheter.

Figure 15:
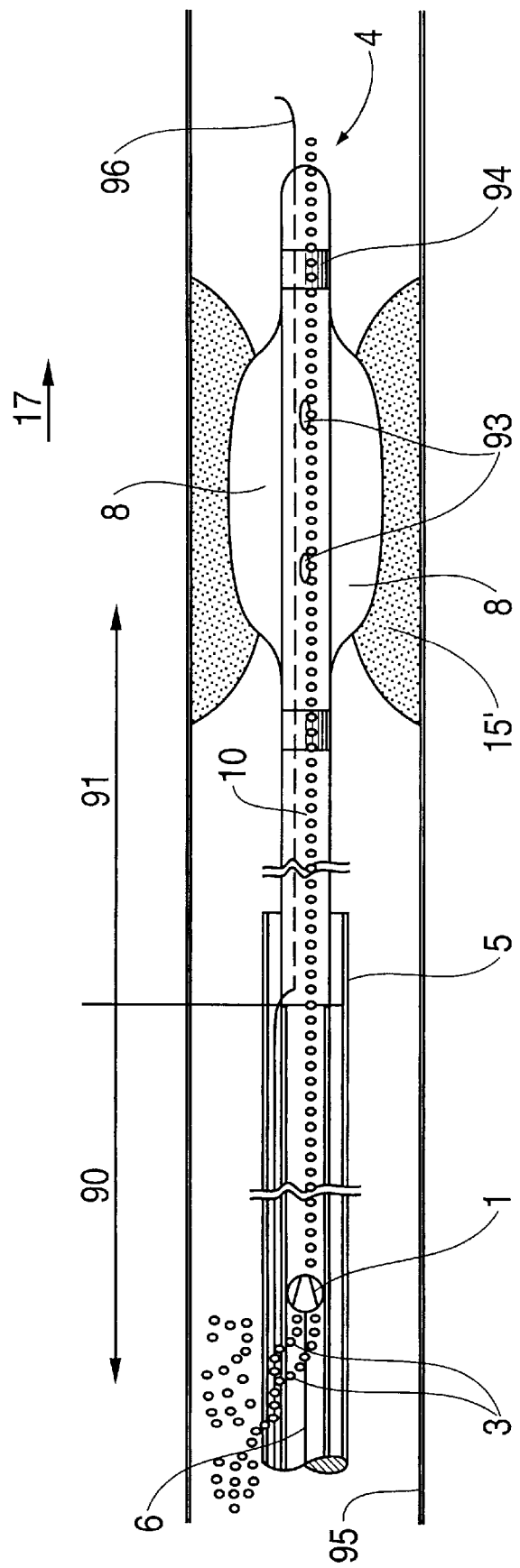
FIG. 15 is a schematic illustration of a pump arrangement according to embodiments of the present invention.

FIG. 15 shows a flow guide system which has a more rigid segment 90 and a more flexible segment 91. The more rigid segment 90 is embedded in the feed hose 5. The pump 1, located in a relatively proximal part, is therefore well supported. The distal part of the flow guide system is in turn supported by the inflated balloons when the device is in the operational state. Also to be seen in this embodiment is the energy or force transmission line 6, which operates the pump 1, as well as inlet openings 3 for the blood which is to be conveyed, and which escapes at the distal end (for example at 4). The catheter is threaded onto a guide wire 96. It is shown in its operational state, with the balloon 8 dilating a stenosis 15'. The inflation openings of the balloon are indicated by 93. The X-ray marking is designated 94. The arrow under 17 indicates the direction of flow of the blood. The blood vessel is designated 95.

The proximal segment of this flow guide system comprises two lumens. The distal segment consists of three lumens, a balloon and perfusion openings distal of the balloon. The lumens of the distal segment are used for receiving the guide wire for inflation of the balloon and also for blood perfusion.

The thread-on area of the flow guide system is situated at the connection point of the two segments. The pump is driven, for example, via a flexible shaft.

Figure 16:
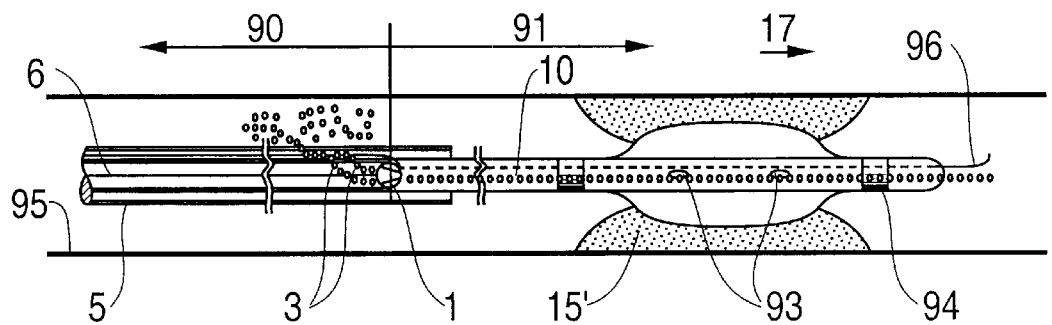
FIG. 16 is a schematic illustration of a modified pump arrangement according to embodiments of the present invention.
Figure 17:
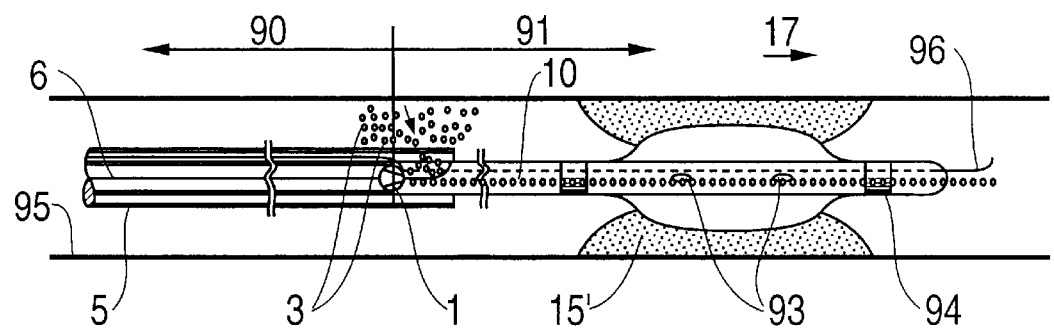
FIG. 17 is a schematic illustration of a modified pump arrangement according to embodiments of the present invention.

FIG. 16 shows a modification of this pump in which the pump position is arranged approximately at the thread-on area of the flow guide system. Here too, the blood is introduced into the shaft on the suction side of the pump and again returned to the blood vessel distally of the balloon. In FIG. 17, by contrast, the inlet location for the blood is arranged on the delivery side of the pump.

Figure 18:
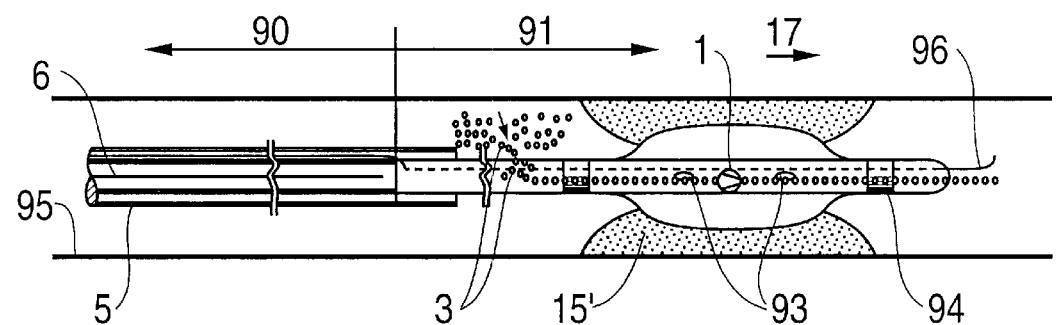
FIG. 18 is a schematic illustration of a modified pump arrangement according to embodiments of the present invention.

The arrangement of the pump, as shown in FIGS. 15 to 17, is preferred for mechanical reasons because of the more solid wall. However, it may sometimes also be desirable for the pump position to be directly under the balloon. Such a modification is shown in FIG. 18. Here, blood is suctioned proximally on the suction side and again released on the delivery side behind the balloon.

Figure 19:
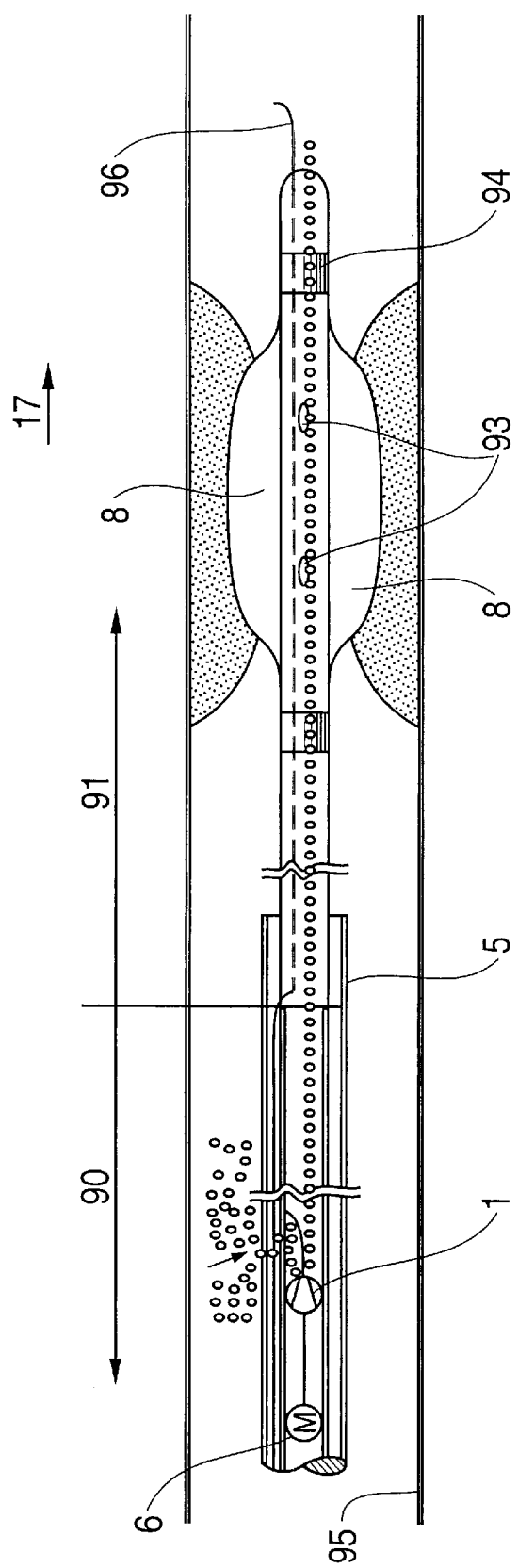
FIG. 19 is a schematic illustration of a pump driving arrangement according to embodiments of the present invention.

FIG. 19 shows an embodiment with a member which is arranged proximal to the pump and which can convert the energy or force of the energy transmission line into mechanical force, this member being connected to the pump via a mechanical force transmission line (e.g. shaft). The member can be a fluidically driveable motor.

In a further embodiment (not shown), the flow guide system has a more rigid segment proximally than distally. Compared to the diameter of the distal part, this segment can have a greater diameter or the same diameter. The more rigid segment is then connected proximally to the feed hose.

Figure 8:
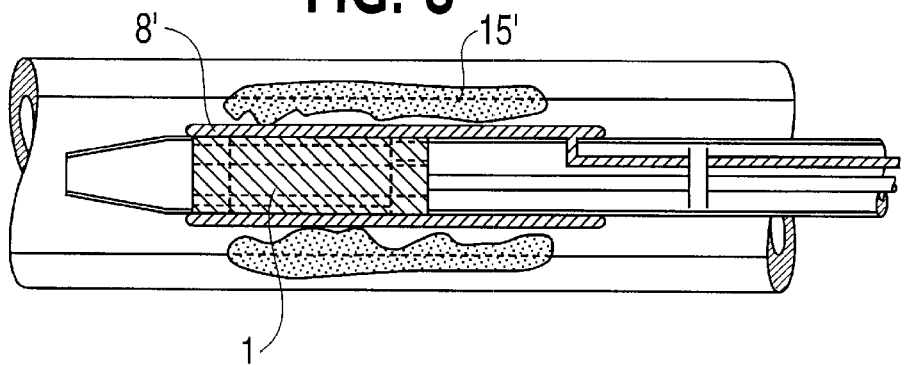
FIG. 8 is an explanatory illustration of how the catheter shown in FIG. 1 can be used for dilation.
Figure 9:
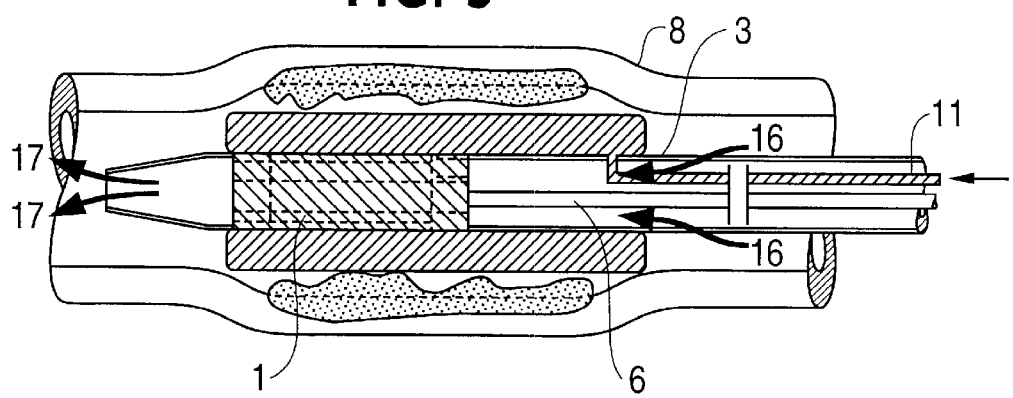
FIG. 9 is an explanatory illustration of how the catheter shown in FIG. 1 can be used for dilation.
Figure 10:
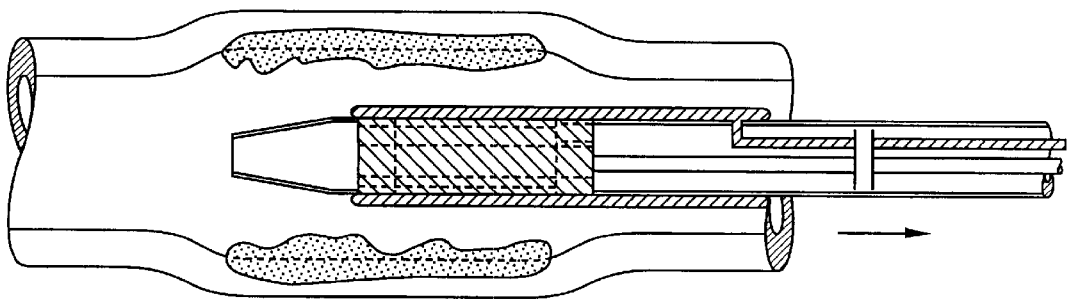
FIG. 10 is an explanatory illustration of how the catheter shown in FIG. 1 can be used for dilation.

FIGS. 8 to 10 illustrate how the catheter can be used: during the balloon dilation, the operational area of the catheter is placed at the site of the constriction (FIG. 8). In accordance with the treatment principle, the balloon is pressurized, while at the same time the pump maintains the bloodstream between the separated vessel areas (FIG. 9). After the treatment, the balloon is made smaller, the pump is switched off and the catheter removed (FIG. 10).

In the figure, reference 15' indicates an obstruction in the blood vessel, for example a deposit.

The dimensions of the dilation catheter should be chosen such that the extent of the artificial bloodstream through the narrowed flow area corresponds as far as possible to the natural bloodstream.

Illustrative Field of Application "Medication Catheter" with Actively Supported Flow of Fluid A field of application for instruments based on such devices is the delivery of medication within vessel systems carrying body fluids, such as blood, lymph, bile or liquor. The object is the targeted delivery of medication to a defined vessel area, such as, for example, the treatment of stenoses, lesions and other indications in vessels. The subject matter of the invention is intended to substantially improve lysis therapy, as used in cardiology, angiology, neuroradiology and other areas, and to permit new forms of treatment for local administration of medication to fluid-carrying vessel systems.

In the area of cardiology and angiology, there are various procedures for removing stenoses and lesions, such as, for example, balloon implantation. Alternative techniques used for removing vessel deposits are also the following treatment forms: bypass operations, vessel transplantations, rapidly and slowly rotating systems with equipped milling head, implants for widening the vessel interior (stents), removal of deposits with the aid of laser angioplasty, ultrasound, atherectomy, systemic treatment with lysing and other locally acting drugs (e.g. growth-inhibiting drugs) or local drug and lysis treatment with the aid of a porous or perforated catheter. All these methods to some extent require a massive intervention, and some of them can only be used with extremely complex medical engineering. Another disadvantage is that the drug is often diluted too quickly at the treatment site by the bloodstream, so that a local mode of action, if not ruled out altogether, is at any rate only very weak. Conversely, in the case of administration of drugs by infusion, too high a concentration (which is necessary to ensure that there are always sufficient concentrations at the treatment site) can produce a toxic effect. In the case of local lysis and other drug applications, the length of time of the drug treatment is mostly very limited.

It is therefore proposed to use, in this field, devices according to embodiments of the present invention, if appropriate in further special embodiments which have already been mentioned above. Working with such a device, it is possible to ensure that local drug and lysis treatment can be carried out in damaged vessel areas without this resulting in an insufficient supply of blood. As a result of the active maintenance of a stream of body fluid during treatment-induced closure of a damaged vessel area, the treatment is not limited in terms of time and is therefore considerably more effective. Furthermore, when carrying out purely local delivery of therapeutic agents, the disadvantages of systemic treatment do not occur, so that it is possible to work with higher doses of therapeutic agents or even new drugs. Thus, working with the device according to embodiments of the invention opens up completely new possibilities for local drug therapy.

The medication catheter according to the invention will be explained below principally with reference to FIG. 11 and further figures, although variable embodiments are of course possible, some of whose features have already been described above. The medication catheter too has a front part which is referred to as the artificial flow guide system 10. Embedded in it is at least one pump 1 which, in a preferred embodiment, can be operated in both directions depending on the nature of the vectorial component, so that the catheter can be advanced to the constriction both in the direction of flow and against the direction of flow in the vessel. The type of pump can also be chosen freely here; the miniaturized gear pumps or vane pumps, centrifugal pumps, hose pumps, diaphragm pumps or balloon pumps already mentioned above are especially possible here. Continuously feeding pumps are substantially preferred. The pump can be chosen in different sizes, with correspondingly variable pumping capacity, for use in different vessel areas.

On the suction side of the pump there is at least one inlet opening 3 for inflowing blood 16; on the delivery side there is at least one outlet opening 4 for outflowing blood 17. The position, form, number and shape of the openings are variable and depend on the envisaged use. In this respect, reference should again be made to the more general statements. The housing 9 has, in the area between the two balances 8, two openings 72, 74 trough which alternately either medication fluid is only delivered. Alternatively, one of the fluids can serve for the delivery of a liquid medicament, while fluid is suctioned through a bypass line from the shut-off vessel space. For said purposes, the two corresponding lines 71 and 73 are connected to a medication pump 75 or to a medication pump and suction pump. The device shown here with two shut-off balloons 8 is an illustrative embodiment.

Alternatively, it is possible for the device to have only one shutoff balloon 8, in which case the admission line for the drug-containing fluid is identical with the pressure generation line 11 for inflating the balloon. In such an embodiment, the balloon has openings through which the drug-containing fluid can escape into the surrounding area. In a further embodiment, the catheter can also have several balloons, which have the same function as the last-described balloon 8.

Figure 11:
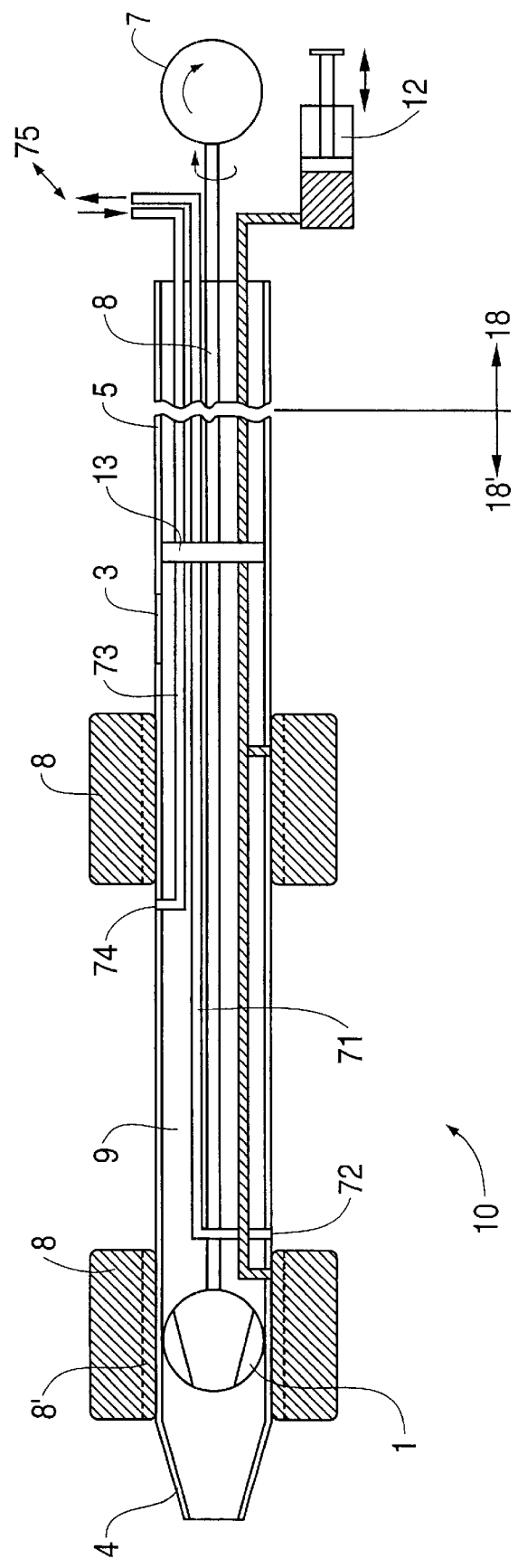
FIG. 11 is a schematic illustration of a catheter according to a further embodiment of the present invention.

The artificial flow guide system 10 in FIG. 11 is also connected integrally to the flexible feed hose 5. The energy or force transmission line 6 runs as far as the pump 1 through the interior of the feed hose 5 from a drive unit 7—not necessarily forming part of the present invention—which, when the catheter is in the operating state, is situated outside the body. The embodiment in FIG. 11 also shows a seal 13 according to embodiments of the present invention, with which seal the lumen of the artificial flow guide system is sealed off in the flexible feed hose. The arrow 18' relates to that part of the catheter which passes into the body, the arrow 18 to those parts which remain outside the body.

Of course, the invention is not limited to dilation catheters with only one pump or with only one balloon. Regarding the arrangement of several pumps, what has already been stated above once again applies.

The flexible feed hose 5 connected to the artificial flow guide system, and the energy or force transmission line arranged therein, have already been described in detail above; the general and specific aspects which were set out there do of course also apply to the dilation catheter.

Figure 12:
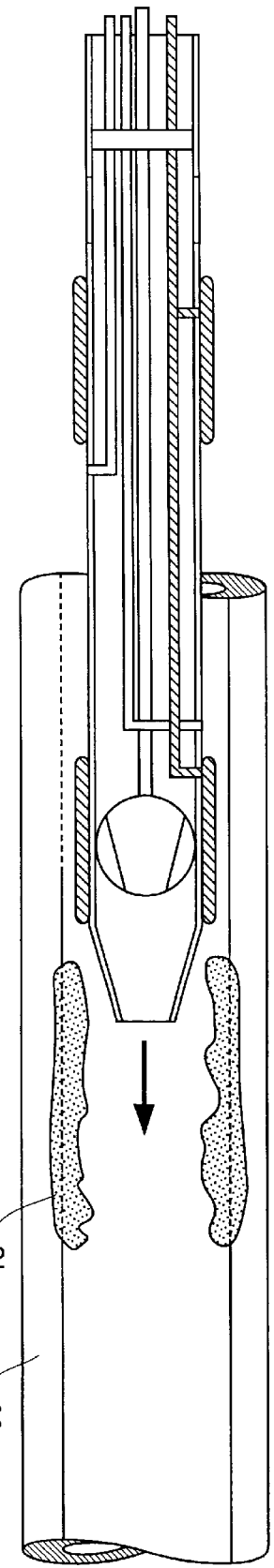
FIG. 12 is an explanatory illustration of how the catheter shown in FIG. 11 can be used for medication delivery.
Figure 13:
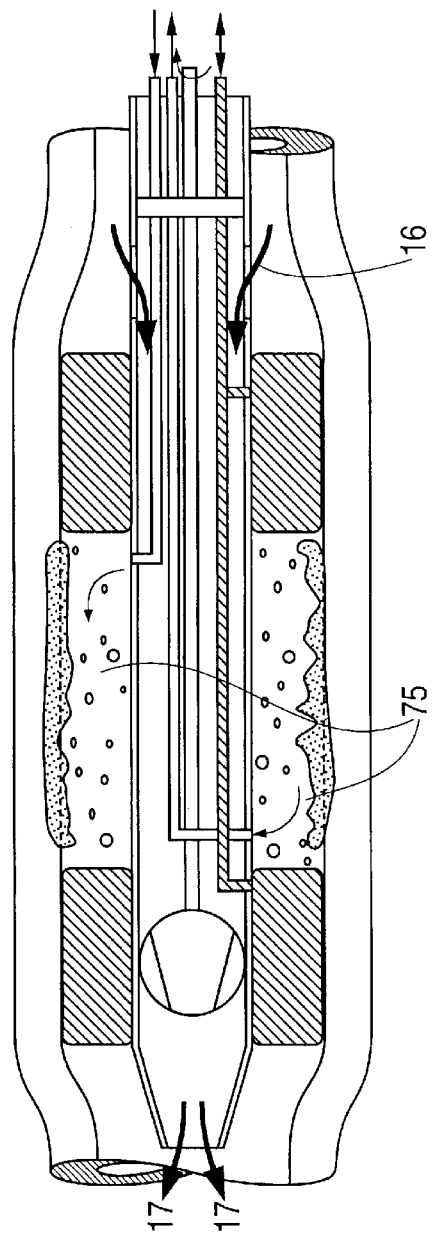
FIG. 13 is an explanatory illustration of how the catheter shown in FIG. 11 can be used for medication delivery.

FIGS. 12 and 13 illustrate how a catheter with two balloons can be used: in drug delivery dilation, the operational area of the catheter is placed at the narrowed site of the vessel. In an embodiment with only one balloon which is perforated or porous, or has other outlet openings, this balloon is pressurized by the outflowing therapeutic agents (not shown). When using two shutoff balloons, these are preferably expanded at the same time in order to shut off as far as possible the vessel area which is to be treated. With this catheter form, higher concentrations of therapeutic agents are possible during treatment. The pump in this case maintains the stream of fluid between the separated vessel areas (see also FIG. 13).

For lysis treatment of deposits in vessels, suitable drugs such as streptokinase, urukinase or rt-PA (plasminogen) or the like are introduced through the admission tubing. The solution concentration of the therapeutic agents is adjusted according to the system design used.

In the drug-based treatment of vascular neoplasms, arteriosclerosis of the vessels, restenosis and other indications, suitable drugs are introduced through the admission tubing. In the double balloon system, the fluid volume of therapeutic agents, body fluid and, if appropriate, detached particles can be suctioned off again in reverse via one of the two fluid lines, which are designated 75 in FIG. 13 and are there intended to symbolize the delivery of drug, and can be replaced by new therapeutic agents. In order to achieve this without the tube collapsing as a result of the acting ambient pressure, an additional medicament pump can be used. This is preferably integrated in the operational area of the catheter. Such a pump could also have the further function of breaking up fairly large detached cell particles. The mode of operation of such a medicament pump can be continuous or intermittent.

After the lyzing drug treatment, the double balloon system also permits subsequent regeneration-supporting treatment.

After the treatment, the balloons are made smaller and the catheter is removed.

Example of a Pump (1) Which Can Be Used According to the Invention

Figure 14:
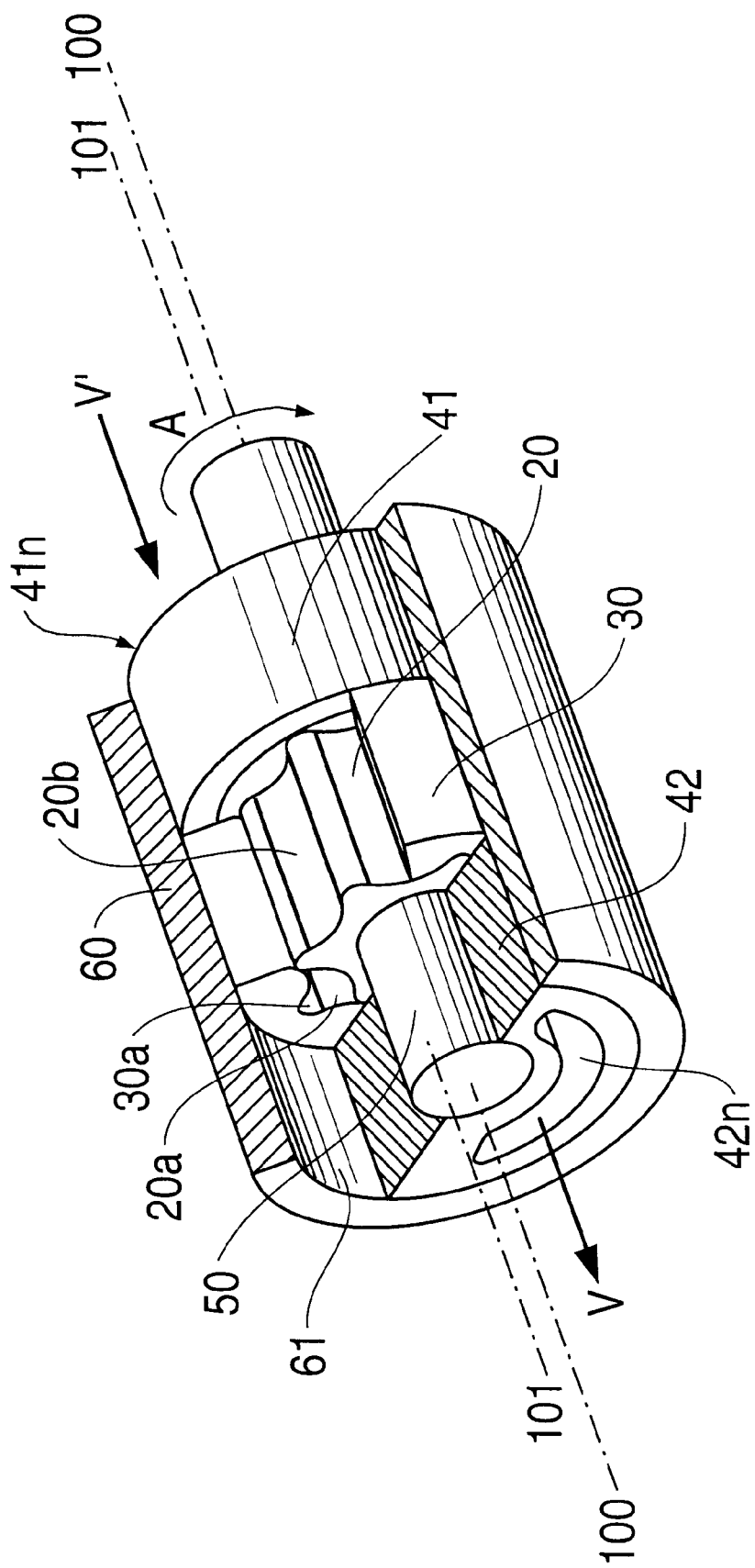
FIG. 14 is a partial cross-section view of a pump for use in embodiments according to the present invention.

FIG. 14 shows a diagrammatic sketch of a pump 1 which has a diameter of the order of preferably under 10 mm, but which, by manufacturing processes of wire spark erosion and cavity sinking, can be reduced to sizes of less than 2.5 mm. The length of the pump is in the latter case about 4 mm, measured in the axial direction 100.

The micropump 1 consists of a casing 60 in which five operational elements are integrated, some of them movably, some of them fixed. At each end face of the casing 60 there is an insert 41 and 42, respectively, (42 half omitted), having an eccentric bore for receiving a pump shaft 50. The bores are flush along a first axis 100 which is slightly radially offset to the outside in relation to the center axis 101 of the casing 60.

The two end inserts 41, 42 are at an axial distance from each other, and between them there are two rotors which rotate with one another and engage in one another, an outer rotor part 30 and an inner rotor part 20. The inner rotor 20 has outwardly directed teeth 20a and grooves 20b distributed at uniform intervals about its circumference. The teeth 20a engage with the outer rotor part 30 which has grooves 30a which open inward and which are distributed circumferentially at uniform intervals and, in their shape, match the teeth 20a in such a way that each tooth 20a of the inner rotor 20 forms an axially directed sealing line on the inner surface of the outer rotor 30. All the sealing lines move in the drive direction A about the axis 100.

The inner rotor 20 describes a rotation movement together with the drive shaft 50, a drive mechanism can couple in a rotary movement A via a longer flexible shaft, an electrical drive mechanism can also be arranged directly on the shaft 50.

While the rotation shaft 50 together with the inner wheel 20 arranged fixedly thereon and the outer wheel 30 are rotatable, the other parts of the micropump—the end inserts 41, 42 and the casing 60 extending along the length of the pump 1—are connected circumferentially to one another in a fixed manner. The shaft 50 is rotatably mounted in the bores of the end inserts 41, 42, and the outer wheel 30 is likewise rotatably mounted in the fixed casing 60. Thus, in the case of a rotary drive via the shaft 50, represented by an angle velocity vector A, both the outer wheel 30 and the inner wheel 20 move with a rotational movement of the sealing lines and simultaneously changing chamber volumes 20a, 30a between the outer wheel and the inner wheel during rotation.

The chamber volumes are here in each case smaller in the direction toward the smallest distance of the axis 100 of the rotation shaft 50 from the casing 60, as a result of which the fluid conveyed in them is subjected to increased pressure, whereas they become larger again on the other side after exceeding the smallest distance between axis 100 and inner jacket surface 61 of the casing 60.

Together with kidney-shaped openings 41n, 42n in the end faces, which are so arranged that their smallest radial width in each case begins at the position at which the distance between the axis 100 and the inner jacket of the casing 60 is at its smallest, whereas their maximum radial width is located at the position which is close to the greatest distance of axis 100 from the inner jacket surface of the casing 60, a feed pump is contained. The inflow kidney, which is situated on the side for the admission of the fluid to be conveyed V', is mounted in the opposite direction to that outflow kidney 42n which, in the figure mentioned, is represented at the outflow position for the delivery volume V being fed under pressure. The figure thus shows on the outflow side an outflow kidney which, in the shown rotational direction A of the pump, widens from the smallest distance of the axis 100 to the greatest distance of the axis 100 from the inner jacket surface 61, while the inflow kidney 41n is situated in the end insert 41 and narrows, in its radial extent, with its greatest radial width from the position of the greatest distance of the axis 100 from the inner jacket surface 61 to the smallest distance of the axis 100 from the inner jacket surface 61 of the casing 60.

The dimensioning and the change in width of the two kidneys are adapted to the following criteria:

The kidneys must be smaller than the corresponding semicircular surfaces of the end inserts 41, 42.

A short circuit of the delivery, i.e. a continuous connection between the inlet kidney and the outlet kidney, is prevented in all positions of rotation.

The inlet and outlet cross section of the kidneys—the change in radial dimensioning—is oriented to the root diameter of the outer wheel 30 and the root diameter of the inner wheel 20, in which case the cross-sectional surface should be chosen as large as possible, in order to maintain slight pressure loss, at any rate maintaining the stated dimension specifications.

The two kidneys can alternatively be incorporated also as curved grooves into the inner flat wall of the end faces, in which case a cylindrical bore is then in each case provided in each case in the axial direction of the pump as outlet and inlet. This increases the stability, which, with the small component sizes, is not unimportant.

A single production of the pump consisting of only six components is possible with the stated wire spark erosion and cavity sinking, in which case all the pump parts can be adequately described with cylinder coordinates, which, for the production, means that one dimension requires no additional working. The end inserts 41 and 42 can be manufactured by wire spark erosion. The shaft 50 is cylindrical anyway, the inner rotor 20 can likewise be manufactured by wire spark erosion, as can the outer rotor 30. The casing 60, finally, is also a pump component, which can be manufactured by wire spark erosion.

If the aforementioned kidney-shaped inlet and outlet grooves are made in the inner sides of the end inserts 41, 42, then cavity sinking can be used for this.

In large batch numbers, plastic or metal injection molding processes can be used. A material which is recommended for the manufacture of the micropump is hard-sintered metal which has a low stress, can easily be worked by wire spark erosion and cavity sinking, and is medically acceptable. If the erosion methods are used, attention must be paid to the electrical conductivity of the material, if a ceramic injection molding process is used—with molds which can be made, for example, by wire spark erosion and cavity sinking—then the electrical conductivity of the material of the micropump is no longer necessary.

The pump described with reference to the figure and to the manufacturing process can be readily used in the above-described devices for actively supporting a flow of fluid. Said drive A can be provided by a thin, flexible shaft. The drive A can be effected by an electric motor, with electrical power line, mounted directly on the pump or at a slight distance therefrom. The drive of the micropump can also be obtained, however, by a motor which is driven by fluid and which is made in the same way and has the same appearance as the described pump, only, with said motor, a fluidic drive via the admission kidney 41n with a tubing is chosen, which tubing is arranged fixedly on the end insert 41.

Since the casing 30 in the fluidic micromotor is arranged fixedly on the outer wheel 30—for example by adhesive bonding or by a matching fit or by a weld or solder connection—the casing 60 is rotated and can transmit its drive force to the drive A of the pump. The pump can be driven—instead of via the shaft 50 with direction of rotation A—also via the casing 60. It is likewise possible to reverse the drive direction in order then to obtain the delivery action of the micropump in a delivery direction from V to V'.

What is claimed is:

1. A device for actively supporting the flow of body fluids, comprising:
   a) an artificial flow guide system with a surrounding wall and an operational area into which a pump is embedded in such a way that the pump bears against the wall of the flow guide system with complete sealing and can transport body fluid from at least one inlet opening situated in the guide system to at least one outlet opening situated in the guide system;
   b) a flexible feed hose connected to the flow guide system; and
   c) an energy or force transmission line extending through an interior of the flexible feed hose and transmitting energy or force substantially continuously to the pump from a drive unit,
      wherein the pump is a miniature gear pump comprising two rotors, wherein one rotor forms an axially directed sealing line with the other rotor.

2. Device according to claim 1, further comprising:
   a drug-containing fluid admission line extending through the flexible feed hose and adapted for fluid communication with a surrounding environment via at least one opening in at least one of the artificial blood flow guide system and a balloon arranged outside the operational area of the artificial blood flow guide system.

3. Device according to claim 2, wherein at least two balloons are arranged outside the operational area of the artificial blood flow guide system, and the drug-containing fluid admission line includes at least one opening between the balloons adapted for communicating a drug-containing fluid to the surrounding environment.

4. Device according to claim 3, additionally comprising: bypass line extending through the flexible feed hose and including at least one aperture proximate to the at least one opening of the admission line, the at least one aperture being connected to a suction pump adapted for withdrawing a fluid from the surrounding environment.

5. Device according to claim 4, wherein the suction pump is arranged inside one of the artificial blood flow guide system and the flexible feed hose.

6. Device according to claim 2, wherein the drug-containing fluid admission line communicates with at least one balloon, the at least one balloon having openings adapted for communicating a drug-containing fluid to the surrounding environment.

7. Device according to claim 3, wherein a suction pump is arranged inside one of the artificial blood flow guide system and the flexible feed hose.

8. Device according to claim 1, wherein a suction side of the pump is arranged distal to the flexible feed hose, and the artificial flow guide system includes an extension beyond the suction side of the pump, and wherein the flow guide system has a smaller diameter in the area of the extension than in the area of the pump.

9. Device according to claim 8, wherein the extension includes flexible tubing.

10. Device according to claim 9, in which a delivery side of the pump is arranged proximal to the flexible feed hose.

11. Device according to claim 1, additionally comprising:
   at least one balloon arranged outside the operational area of the artificial flow guide system, the at least one balloon being pressurized via a pressure generation line guided through the interior of the flexible feed hose.

12. Device according to claim 5, further comprising:
   an extra-corporal pressure introducing a fluid into the at least one balloon via the pressure generation line.

13. Device according to claim 1, additionally comprising:
   a member arranged proximal to the pump and converting energy or force from the energy transmission line into mechanical force, the member being conncected to the pump via a mechanical force transmission line.

14. Device according to claim 13, in which the member is a motor driven electrically, electro-magnetically or by fluidics.

15. Device according to claim 1, wherein the drive unit includes an extra-corpeal drive unit.

16. Device according to claim 1, wherein the artificial flow guide system includes a lumen providing for the flow of blood, the lumen being sealed off from the flexible feed hose.

17. Device according to claim 1, additionally comprising:
   a guide wire extending to the outlet opening of the flow guide system, the guide wire being rigid in the axial direction but otherwise easily deformable.

18. Device according to claim 1, wherein force is transmitted with a flexible shaft.

19. Device according to claim 1, wherein the artificial flow guide system includes a perforated housing on a suction side of the pump.

20. Device according to claim 1, wherein a plurality of the pumps are coupled fluidically in parallel and are arranged physically one after the other in the artificial flow guide system.

21. Device according to claim 1, wherein the artificial flow guide system includes an extension on a delivery side of the pump, and the extension includes flexible outflow tubing.

22. Device according to claim 1, wherein, at least a short distance before the pump, the energy or force includes a vectorial component defining the suction side and delivery side of the pump, and the vectorial component is reversible in direction.

* * * * *